United States Patent [19]

Hudrlik

[11] Patent Number: 5,265,603
[45] Date of Patent: * Nov. 30, 1993

[54] ELECTRONIC CAPTURE DETECTION FOR A PACER

[75] Inventor: Terrence R. Hudrlik, Fridley, Minn.

[73] Assignee: Medtronic, Inc., Minneapolis, Minn.

[ * ] Notice: The portion of the term of this patent subsequent to Oct. 20, 2009 has been disclaimed.

[21] Appl. No.: 626,061

[22] Filed: Dec. 12, 1990

[51] Int. Cl.⁵ .......................................... A61N 1/362
[52] U.S. Cl. ........................................ 607/9; 607/28
[58] Field of Search ................... 128/419 D, 319 PG

[56] References Cited

U.S. PATENT DOCUMENTS

| | | | |
|---|---|---|---|
| 3,057,356 | 10/1962 | Greatbatch | 128/419 PG |
| 3,345,990 | 10/1967 | Berkovits | 128/419 PG |
| 4,305,396 | 12/1981 | Wittkampf et al. | 128/419 PG |
| 4,729,376 | 3/1988 | DeCote, Jr. | 128/419 PT |
| 4,759,366 | 7/1988 | Callaghan et al. | 128/419 PG |
| 4,858,610 | 8/1989 | Callaghan et al. | 128/419 PG |
| 4,878,497 | 11/1989 | Callaghan et al. | 128/419 PG |

OTHER PUBLICATIONS

Biology of the Uterus, edited by Ralph M. Wynn pp. 466-481, publication date unknown.
"Voltage-Clamp Studies on Uterine Smooth Muscle" by Nels G. Anderson, Jr. published in the Journal of General Physiology, vol. 54, No. 2, Aug., 1969 pp. 145-165.
"The Action Potential in the Smooth Muscle of the Guinea Pig Teania Coli and Ureter Studied by the Dougle Sucrose-Gap Method" by H. Kuriyama, et al. published in The Journal of General Physiology, vol. 55, No. 2, Feb. 1970.

Primary Examiner—William E. Kamm
Assistant Examiner—Scott M. Getzow
Attorney, Agent, or Firm—Reed A. Duthler; Harold R. Patton

[57] ABSTRACT

A pacemaker sense amplifier which includes active circuitry which establishes and attempts to maintain a constant field density between two electrodes, effectively clamping them together at substantially fixed relative electrical potentials. The amount of current or power provided to the electrodes monitored and forms the basis of detection of the passing cardiac depolarization wavefront. A timer is sued to define a detection window after the generation of a pacing pulse. The occurrence of a detected depolarization within the detection window is indicates that the pacing pulse has captured the heart.

12 Claims, 5 Drawing Sheets

ELECTRONIC CAPTURE DETECTION FOR A PACER

BACKGROUND OF THE INVENTION

This invention relates to implantable pacemakers and more particularly to a system for detecting the evoked response of the cardiac tissue shortly after the application of an electrical stimulation pulse.

DESCRIPTION OF THE PRIOR ART

The cardiovascular system provides oxygenated blood to various structures of the body. The body's demand for oxygenated blood is reflected by the rate at which the sinus node of the heart beats. The electrical signal generated by the sinus node causes the atria or upper chambers of the heart to contract, forcing blood into the lower chambers or ventricles of the heart. After a brief delay, the lower chambers of the heart contract forcing the blood through out the body. The contraction of the ventricles proceeds in an organized fashion which is reflected by the passage of a depolarization wave front through the heart muscle.

Various disease mechanisms cause conduction disturbances which interfere with the natural conduction system of the heart. A variety of implantable medical devices have been developed to treat these abnormalities. The bradycardia pacemaker is an example of one such implantable medical device which supplies therapeutic stimulation to the heart to compensate for these conduction defects.

The modern pacer system comprises a catheter or lead system, and a pulse generator or pacer. The lead system is passed through a vein into the right ventricle of the heart. There are two forms of lead systems in common use. The first form is the unipolar lead which has a tip electrode located proximate the distal end of the lead. The pacer can forms the reference electrode in this configuration. The second form of lead system is the bipolar lead which includes a tip electrode used in conjunction with a ring electrode located near the tip electrode. In either case the distal end of the lead carries a tip electrode which contacts the myocardium. The proximal end of the lead is connected to the pacer or pulse generator. The pulse generator is usually implanted subcutaneously outside the rib cage.

The first pacemakers paced the heart at a metronomic rate independent of the hearts underlying rhythm. Such pacemakers are typified by U.S. Pat. No. 3,057,356 to Greatbatch. One problem with such pacemakers is that they may compete with the heart's underlying rhythm and provoke lethal arrhythmias.

The demand pacer was introduced to overcome this defect. This form of pacer contains circuitry to detect the depolarization of the cardiac tissue. The circuitry for performing this function is referred to as a sense amplifier in this art. The function of the sense amplifier is to generate a sense event signal which is used by the escape interval timer of the pacer to synchronize the pacer to the hearts rhythm. In operation the pacer escape interval timer is set to a nominal stimulation rate which reflects the lowest permissible heart rate. If the underlying heart rate is above this standby rate the pacer detects the cardiac depolarization and prevents the delivery of pacing stimuli. This form of pacer is now classified as a VVI mode pacer and is taught to the art by U.S. Pat. No. 3,345,990 to B. Berkovits. The efficacy and safety of this pacing modality requires a reliable sensor of heart activity.

In an effort to extend the useful operating life of pacemakers and to allow extraction of useful diagnostic information, it has been common in recent years to provide a programmable output stimulation pulse which permits the physician to select an output pulse energy which is known to be sufficient to capture the heart but which is below the maximum obtainable output energy. In operation the physician can conserve battery power and thus extend the useful life of the pacer by selecting an output pulse energy just above the stimulation threshold of the patients heart.

It has also been proposed to automatically adjust the output energy level. U.S. Pat. No. 4,305,396 issued to Wittkampf teaches a pacer in which the pacemaker has its output energy automatically controlled in response to the detection of driven R-waves and its pacing rate varied as a function of the energy required to capture the heart. Practical realization of such systems has not occurred, because the pacer output stimulus which is delivered to the lead system is many orders of magnitude larger than the electrical signal generated by the heart and can mask detection of the driven or stimulated R-wave. However this reference illustrates the long standing desire for a practical detector system capable of reliably sensing a stimulated R-wave.

SUMMARY OF THE INVENTION

In contrast to the approach taken by the prior art, the present invention utilizes a low impedance field density clamp sense amplifier which uses active detection circuitry to monitor the amount of current supplied to the selected sensing electrode. The supplied current changes the surface charge density to compensate for the electrode-electrolyte disturbance caused by the passage of a cardiac depolarization wavefront. This form of sensing is most sensitive to changes in charge distribution in a small volume of tissue located adjacent to the electrode. This form of sensing therefore is not strongly affected by far-field events, in contrast to high impedance biologic sense amplifiers.

Timer circuits coupled to the stimulating and detection circuits cooperate to define a capture detection time window, referred to as "T2", initiated shortly after the delivery of a pacing pulse. A cardiac depolarization occurring within this time window is identified as a driven R-wave. The occurrence or non-occurrence of a driven R-wave following a pacing pulse may be used to provoke a state transition in the pacer to alter its operation. For example, the amplitude or width of the pacing pulse may be adjusted to provide reliable pacing at the minimum appropriate pulse energy level. Alternatively the occurrence of the driven R-wave may be used for diagnostic purposes.

In a preferred embodiment of the pacer described herein, the detection of a driven R-wave is used to control the stimulation energy delivered by the pacer output stage. In general, the auto-threshold pacer disclosed will minimize its output energy to maximize pulse generator longevity.

BRIEF DESCRIPTION OF THE DRAWINGS

In the drawing, like reference numerals indicate corresponding structures throughout the several views in which:

FIG. 6 is a state machine description of the procedure for detecting the driven R-wave.

DETAILED DESCRIPTION OF THE PREFERRED EMBODIMENT

In the following description, reference is made to an illustrative embodiment for carrying out the invention. It is understood that other embodiments may be utilized without departing from the scope of the invention. For example, the invention is disclosed in the context of a VVI modality pacer for treating bradycardia. It should be appreciated that the technique for myocardial depolarization detection could also be applied to a dual chamber device where capture detection is used to control the energy of the pacing stimuli delivered to the atria. In a similar fashion the ability to detect the driven R-wave will find utility in tachyrhythmia pacers where direct evidence of capture can be used as feedback to control the delivery of tachyarrhythmia therapies.

Figure 1:
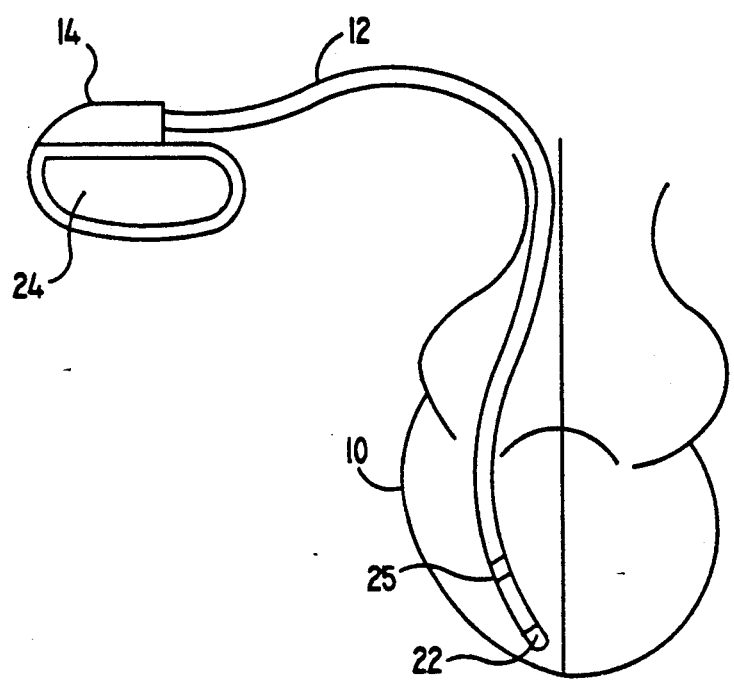
FIG. 1 is a schematic diagram depicting the interconnection between the pacer and the heart.

FIG. 1 is a schematic representation of an implanted pacer. In the figure, the pacer 14 is implanted subcutaneously, between the skin and the ribs. A lead 12 is passed through a vein into the right ventricle of the heart 10. The distal end of the lead or catheter has a tip electrode 22 contacting the interior of the heart. A second, ring electrode 25, is spaced from the tip electrode 22. Each of these electrodes is connected to the circuitry contained in the pacer 14. A portion of the metallic enclosure or "can" of the pacer forms an electrode surface 24.

This electrode configuration places tip electrode 22 and ring electrode 25 within the heart. The remaining, can electrode 24, is outside the heart. The distance between the tip electrode 22 and the ring electrode is typically between 10 and 30 mm and the distance between the ring electrode 25 and the pacer can electrode 24 is typically between 10 and 30 cm.

Although a variety of lead configurations can be used to pace the heart and to sense the intrinsic depolarizations of the heart, the present invention is disclosed in the context a unipolar pacing configuration where the pacing energy is delivered between the tip electrode 22 and the can electrode 24. Sensing is accomplished between the ring electrode 25 and the can electrode 24. Alternative electrode configurations include those in which only one pair of electrodes are used, coupled to both the sense amplifier and the pulse generator and those in which two pairs of electrodes are used, one pair coupled to the sense amplifier and the other pair coupled to the pulse generator. Electrode pairs may include two electrodes located on or in the heart, or one electrode located in or on the heart and one electrode located displaced from the heart. The sense amplifier may also be employed using two electrodes, both located remote from the heart, for example both located on the pacemaker can.

Figure 2:
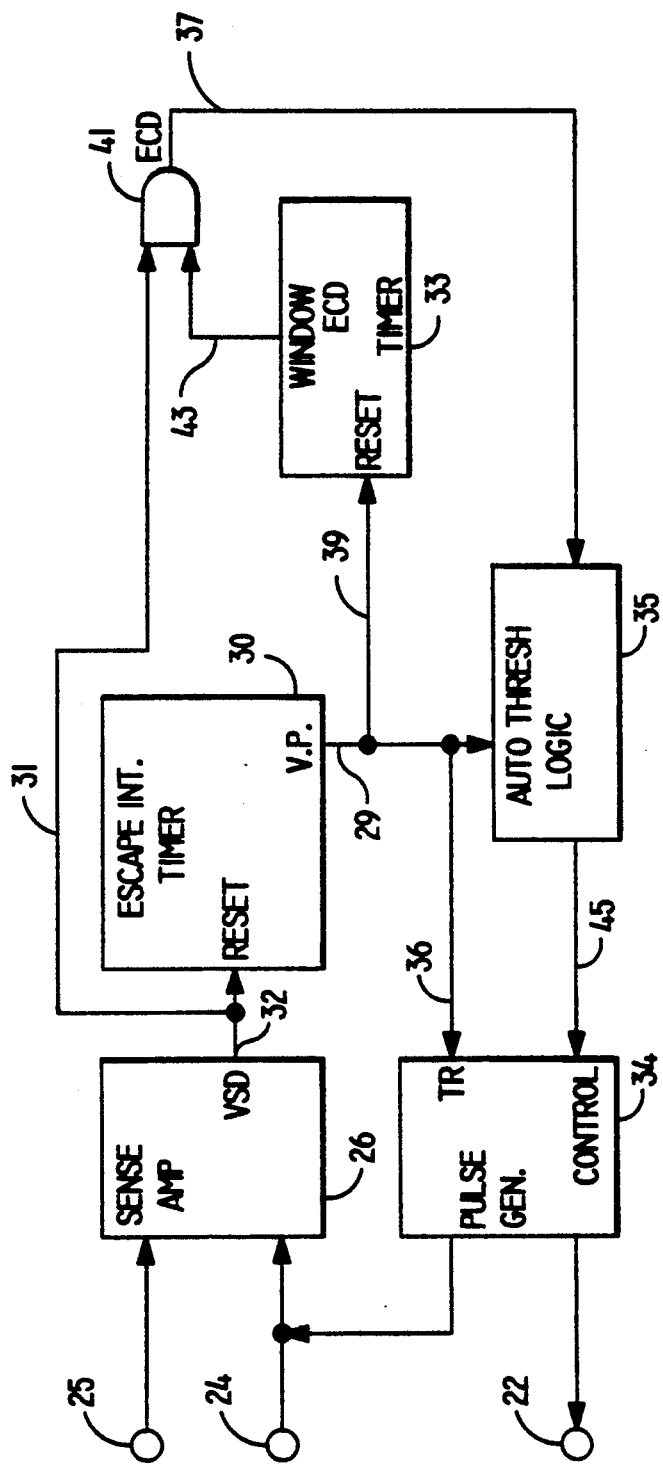
FIG. 2 is a block diagram depicting the relationship between the sense amplifier and the other pacer circuitry.

FIG. 2 depicts the major circuit elements contained within the pacer. For detection of ventricular depolarizations, it is preferred to couple the sense amplifier 26 to sense electrical heart signals between the ring electrode 25 and the can electrode 24. The pacing pulse generator 34 is preferably connected to pace between the tip electrode 22 and the can electrode 24.

In operation, the sense amplifier 26 detects the occurrence of a cardiac depolarization by means of the ring and can electrodes 25 and 24, and in response generates a ventricular sense detect signal (VS detect) on line 32. The occurrence of a VS detect signal resets the escape interval timer 30 and thus resynchronizes the pacer to the underlying rhythm of the patients heart. If no ventricular depolarizations are sensed within the escape interval, timer 30 generates a ventricular pace signal on line 29 at the expiration of the escape interval. The ventricular pace signal (V-pace) is provided to the pulse generator circuit 34 via line 36. Typically, the escape interval timer 30 is remotely programmed by telemetry to adjust the duration of the ventricular escape interval, which corresponds to the desired maximum time interval between heartbeats.

The V-pace signal on line 36 generated by the escape interval timer 30 is also communicated to electronic capture detect timer 33 via line 39. The V-pace signal resets the timer 33, which thereafter defines the capture detect time window. During the capture detect window (T2), timer 33 provides a signal on line 43 which enables gate 41. The occurrence of a VS detect signal during the capture detect window results in a capture detect signal (ECD) from gate 41 on line 37.

In the case of a typical modern pacemaker, the duration of the pacing pulse may be about 1 ms, with a fast recharge pulse thereafter extending for about 8 ms. In such case, the capture detect window can begin approximately 10 ms after the ventricular pacing pulse and may end 40 to 50 ms thereafter. In cases where shorter pacing and recharge pulse widths are used, the capture detect window may begin sooner. The given values have been found to work well with the conduction velocity (1 mm/msec) found in canine models. The conduction velocities found in humans range from 0.5 mm/msec to 2 mm/msec. It is anticipated that each of these values will be programmable with nominal window lengths of up to 80-100 ms to provide performance with a wide range of conduction velocities occurring in the human population. The time interval from ventricular pacing pulse to the start of the electronic capture detect window is referred to as T1. At the expiration of T1, the capture detect window T2 begins.

As previously described, a capture detect signal is generated when the sense amplifier 26 generates a VS-detect signal during the capture detect window T2. This capture detect signal may be used in a variety of ways, and is illustrated in the context of an auto-threshold type pacer. In this instance, the capture detect signal ECD is communicated to auto-threshold logic 35 via line 37. Auto-threshold logic 35 controls the energy content of the pacing pulses delivered by the pulse generator 34 to the lead system. In the event that a pacing pulse is delivered and no capture detect signal follows, auto-threshold logic 35 will generate a control signal on line 45 to increment the amplitude of the pacing pulses provided by pulse generator 34. Auto-threshold logic 35 may also decrement the amplitude of the pacing pulses in response to an extended period in which all pacing pulses successfully capture the heart to enable a determination of the minimum energy required to reliably pace the heart. Auto-threshold logic 35 may also respond to the failure of a pacing pulse to capture the heart by quickly triggering an additional pacing pulse at an increased amplitude.

Appropriate mechanisms for adjusting the energy content of the pacing pulses generated by pulse generator 34 are disclosed in U.S. Pat. No. 4,858,610 issued to Callaghan et al, U.S. Pat. No. 4,878,497 issued to Callaghan et al. and U.S. Pat. No. 4,729,376 issued to DeCote, all of which are incorporated herein by reference in their entireties. Alternative pacing functions which may be modified in response to the detection or non-detection of cardiac depolarizations during the capture detect window are described in U.S. Pat. No. 4,795,366 issued to Callaghan et al., and in the above cited U.S. Pat. No. 4,305,396 issued to Wittkampf, both of which are incorporated herein by reference in their entireties.

Figure 3:
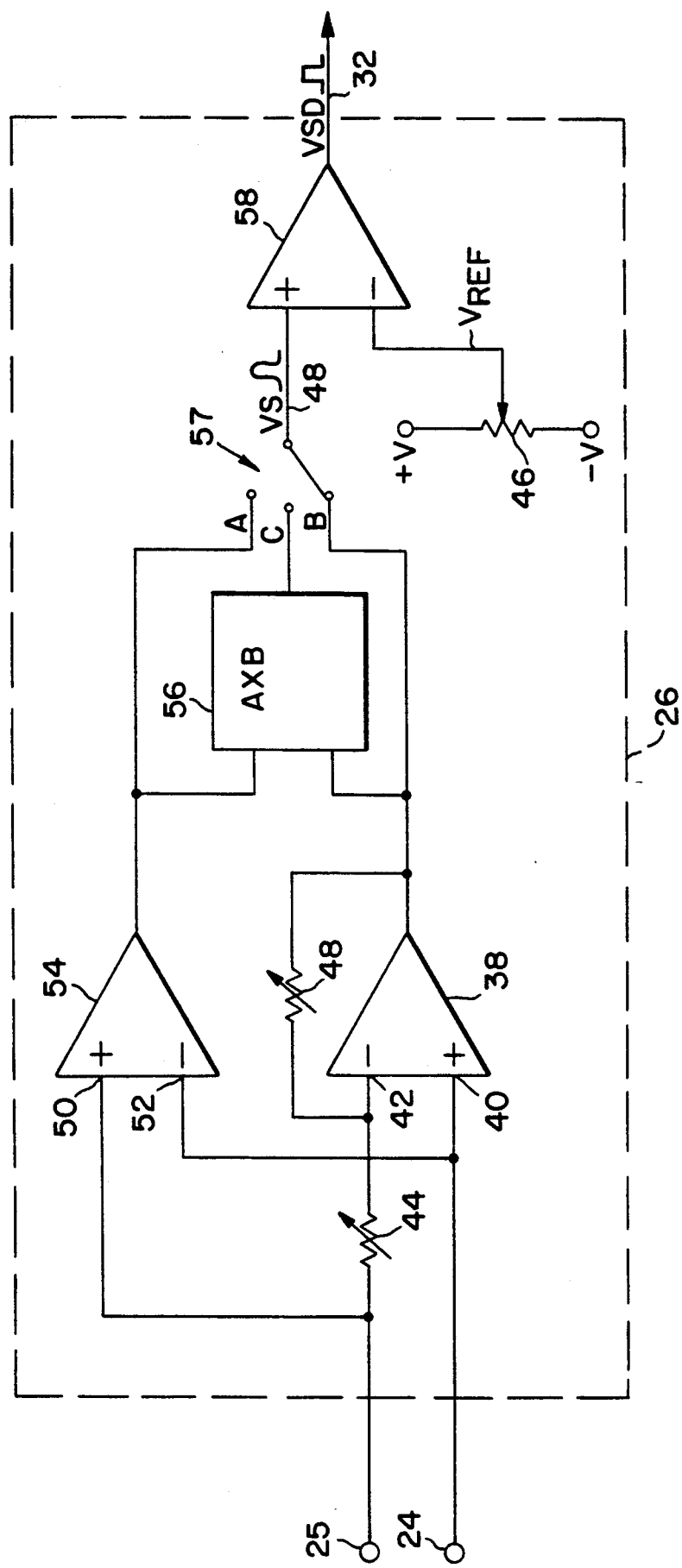
FIG. 3 is a schematic diagram of an illustrative circuit for implementing the sense amplifier portion of the invention.

FIG. 3 discloses a preferred sense amplifier for use in conjunction with the electronic capture detection system. This form of sense amplifier is more fully described in co-pending U.S. patent application Ser. No. 566,636 for a "Field Density Clamp for Sensing Cardiac Depolarizations", filed Oct. 8, 1990, by Hudrlik, which is incorporated by reference herein in its entirety. The active circuitry of the sense amplifier 26 attempts to maintain an equilibrium condition between the sensing electrodes. The field perturbation caused by the passing wavefront is nulled out by the active circuitry which attempts to maintain a fixed relationship between the potentials at the electrodes.

Current supplied to the electrodes in the attempt to maintain an electrode/electrolyte equilibrium condition is passed through a virtual load. The current delivered through the virtual load is monitored and forms the basis for the detection of the passing depolarization wavefront. It is preferred to also monitor the voltage across the virtual load and multiply it with the current measurement to characterize the power delivered to the electrode system in response to the passing depolarization wavefront. Thus, in a preferred embodiment, the cardiac depolarization is distinguished from noise based upon the power level of the depolarization signal. Although this form of sense amplifier is disturbed both by the delivery of pacing energy to the lead system and by the recharge of the output capacitor, the system recovers very quickly.

As shown in the schematic diagram of FIG. 3, the sense amplifier may be practiced with a first operational amplifier 38 which has its non-inverting input 40 connected to the can electrode 24. The inverting input 42 is coupled to ring electrode 25 through a variable resistor 44 which is used to set a virtual load resistance for the system. This resistance is preferably between 10 and 1000 ohms. A feedback path is provided for the amplifier 38 by a resistance 48 which converts input current to a proportional voltage signal B. In operation the op amp 38 provides a signal B which reflects the amount of current provided to electrodes 25 and 24 in the attempt to counteract the perturbation of the electric field surrounding the electrodes due to cardiac depolarization.

A differential amplifier 54 may be provided to measure the magnitude of the potential difference between electrodes 22 and 25, and thus the voltage across the virtual load resistance 44. The non-inverting input 50 of this differential amplifier 54 is coupled to ring electrode 25 while the can electrode 24 is coupled to inverting input 52. The voltage output A of differential amplifier 54 is proportional to the voltage difference between the electrodes 25 and 24. The voltage measurement A and the current measurement current B may be used to compute the power delivered through the virtual load resistance to maintain the constrained equilibrium, as this equilibrium is perturbed by the passage of a cardiac depolarization wavefront. However it is possible to use the current signal B, alone to detect the depolarization.

The power computation is carried out by an analog multiplier 56 which computes the power level an provides a voltage output C proportional to the computed power. Current signal B or power signal C are communicated to comparator 58 via switch 57. Comparator 58 compares the selected input to a threshold voltage VREF defined by voltage source 46. If the selected one of the current signal B or the power signal C exceeds Vref, comparator 58 generates a V-sense detect signal VSD on line 32.

Figure 4:
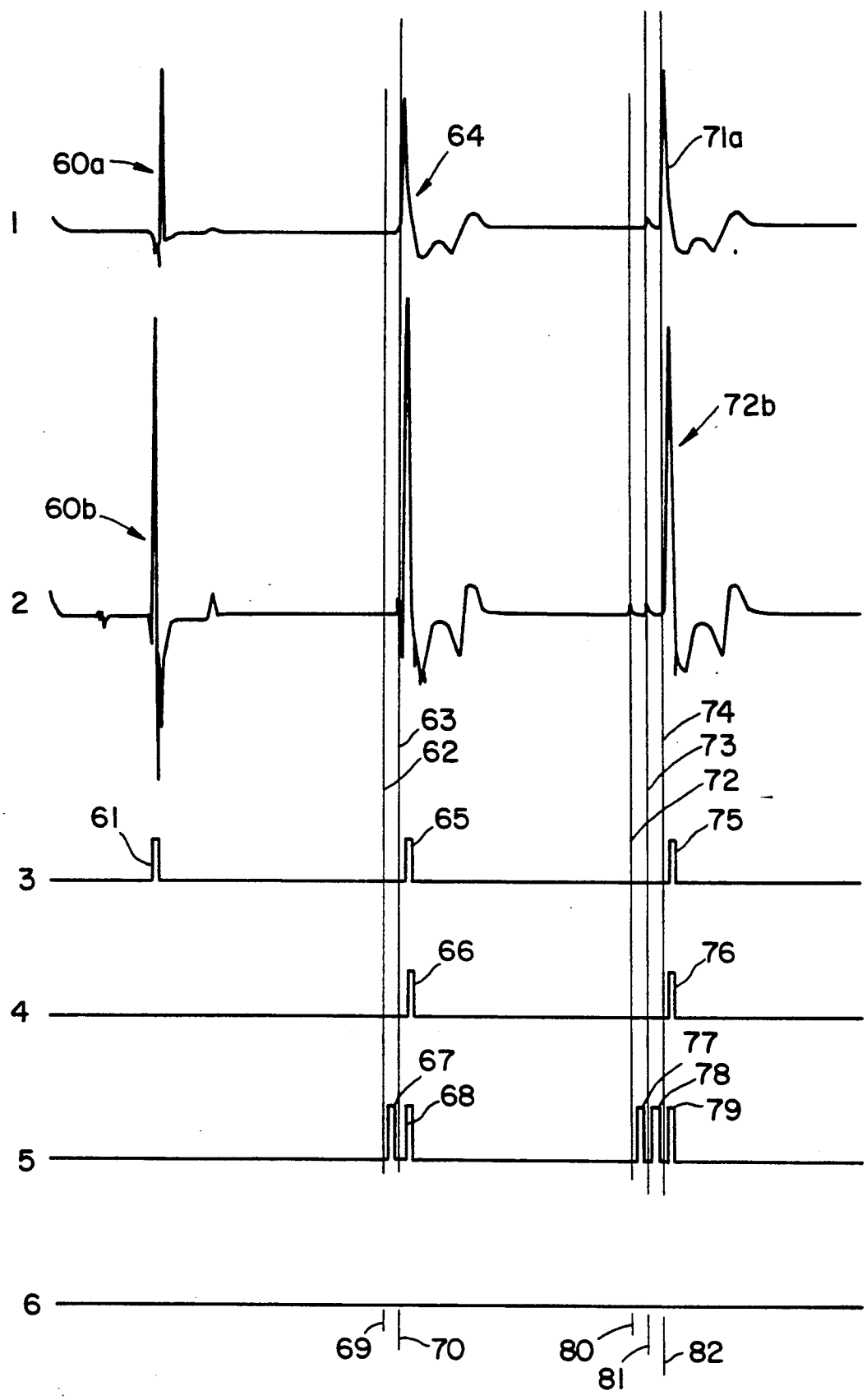
FIG. 4 is a timing diagram which reflects data obtained by testing the invention.

The operation of the invention is illustrated in FIG. 4. This figure shows Tracings of cardiac waveforms collected from a canine subject having a chronic bipolar pacing lead implanted in the heart. Pacing pulses were delivered between the tip electrode and an electrode corresponding to can electrode 24 (FIG. 2). Tracings 1 and 2 were taken with a circuits corresponding to FIG. 3 in which the current signal B was provided to the comparator 58. When the measured current exceeded the sensing threshold (Vref), comparator 58 provided a short, high logic level pulse.

Tracing 1 was taken with a sense amplifier coupled to tip and can electrodes, and corresponds to the current signal B from operational amplifier 38 (FIG. 3).

Tracing 2 was taken with a sense amplifier coupled to the ring and can electrodes and similarly corresponds to the current signal B from operational amplifier 38.

Tracing 3 reflects the logic level output of the sense amplifier and corresponds to the signal taken from the output comparator 58.

Tracing 4 is corresponds to the logic level output of gate 41 (FIG. 3) and indicates the occurrence of a sensed ventricular depolarizations during the T2 time window established by the capture detect timer 33. High logic signals in tracing 4 correspond to capture detect signals from gate 41.

Tracing 5 corresponds to the signal on line 43 from capture detect timer 33 (FIG. 3). High logic level signals in tracing 5 correspond to the duration of the capture detect window T2.

Tracing 6 corresponds to the output of the ventricular pulse generator 34 (FIG. 2). The amplitude of the pacing pulses is reflected by the height of the pulse markers. The occurrence of pacing pulses is also reflected by the sensed artifacts 62,63,72,73 and 74, which extend across tracings 1–5.

The first cardiac waveform 60a, 60b results from a normal sinus depolarization of the heart. V-sense detect signal 61 on tracing 3 reflects the normal detection of this event. In the context of the pacer of FIG. 2, this detected depolarization resets the escape interval timer 30. At the conclusion of the escape interval, timer 30 generates a V-pace signal which triggers a ventricular pacing pulse.

Artifact 62 and pacing pulse marker 69 on tracing 6 indicate the delivery of a pacing pulse. A capture detect window is defined thereafter as indicated at 67, on tracing 5. No depolarization results, as the pacing pulse is of insufficient amplitude to capture the heart. This lack of capture is evidenced by the fact that no V-sense detect signal follows the delivery of the pacing pulse at 62. In this instance the auto-threshold logic 35 (FIG. 2) generates another ventricular pacing pulse as indicated by artifact 63. The amplitude of this pacing pulse is increased, as indicated by pacing pulse marker 70 in tracing 6.

In this instance the second pacing pulse captures the heart as evidenced by the depolarization waveform 64a, 64b on tracings 1 and 2, respectively. This ventricular depolarization was detected within the capture detect window 68 following the delivery of pacing pulse at 63, as evidenced by V-sense detect signal 65 in tracing 3 and capture detect signal 66 in tracing 4.

The tracings associated with depolarization waveform 71a, 71b illustrate a sequence of three pacing pulses delivered at 72,73,74. The first two pacing pulses fail to capture the heart, as indicated by the absence of V-sense detect signals and capture detect signals during capture detect windows 77 and 78. Pacing pulse amplitude is increased with each pulse, as indicated by pacing pulse markers 80,81,82. The third pulse delivered at 74 is successful in capturing the heart as indicated by V-sense detect signal 75 and capture detect signal 76 during capture detect window 79.

The test data shown in FIG. 4, was taken with an experimental version of the invention which permitted adjustment of the T1 and T2 periods. The T1 period extends from the conclusion of the ventricular pace signal depicted in the figure by pacing artifacts 62,63,72,73 and 74. The duration of the T1 period should be short and experimentation suggests that in systems employing field density clamp sense amplifiers, 5–10 ms is an appropriate value. The duration of period T2 should be long enough to allow detection of any pacemaker triggered depolarization. Experimentation suggests that 30–100 ms is an appropriate duration for T2.

Figure 5:
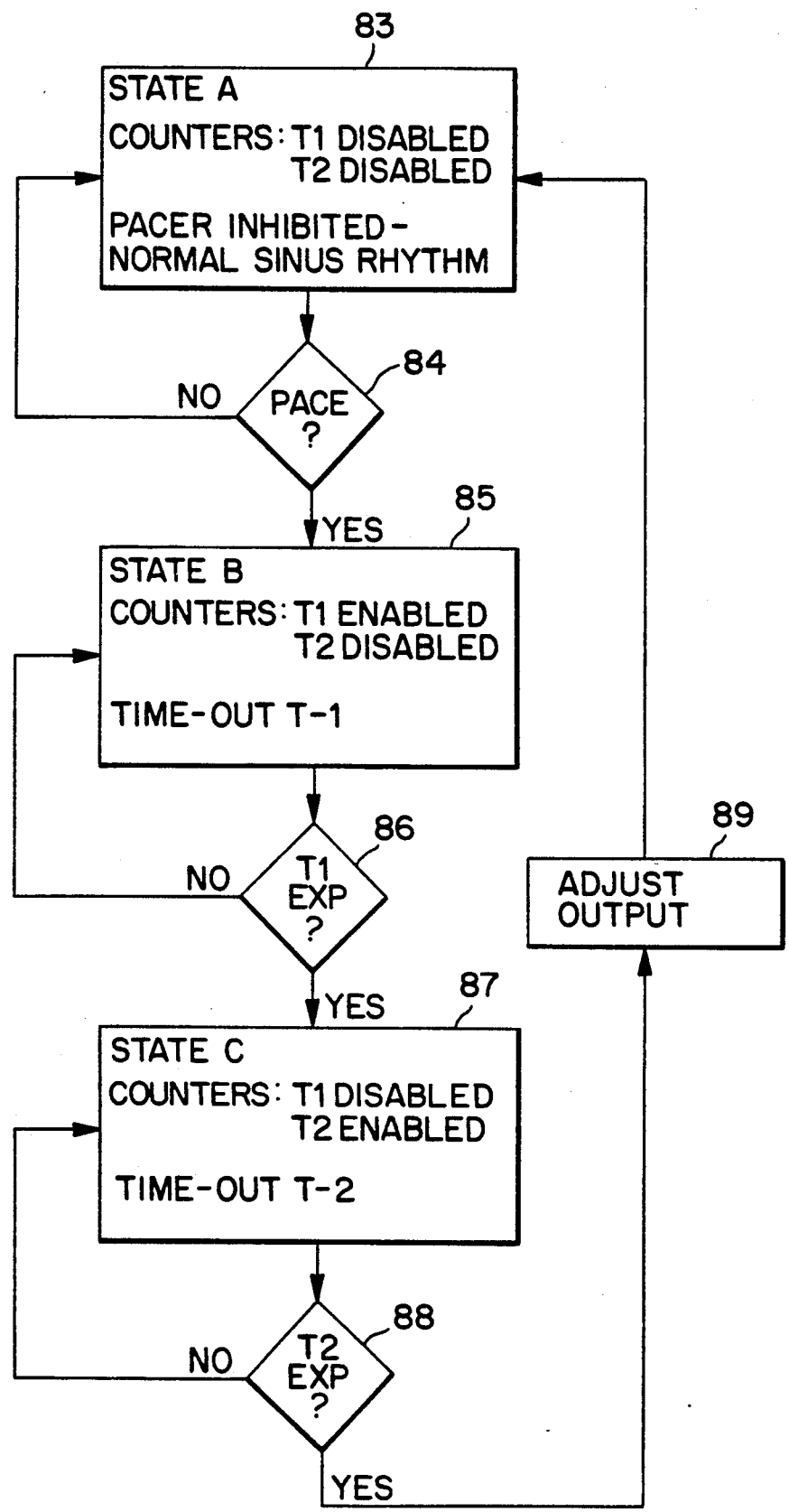
FIG. 5 is a flow chart description of a procedure for generating the driven R-wave detection.

FIG. 5 shows a hardware flow chart setting forth a state machine description of the detection procedure performed by the circuitry of FIG. 2.

In state A shown in the flow chart at 83, both the T1 and T2 timing functions of the ECD timer 33 are disabled. This state corresponds to the pacer's operation during sinus rhythm which inhibits the pacemaker. The state is reentered upon the occurrence of a V-sense detect signal as at 61 in tracing 3.

The occurrence of a V-pace signal at decision block 74 forces a state transition to state B where the T1 timing function is enabled. As the period T1 times out the machine moves from state B (85) to state C (87) where the T2 time window is being timed. If a V-sense detect signal occurs during T2 it is taken as the indication of a driven R-wave, and a capture detect is declared in block 87. The expiration of the T2 time period, tested at decision block 88, triggers adjustment of the pacing pulse amplitude at 89 and the return to state A.

What is claimed is:

1. Apparatus for detecting a depolarization cardiac tissue evoked by a packing pulse, comprising:
   a pulse generator for generating pacing pulses;
   means for applying said pacing pulses to the heart;
   first and second electrodes for sensing cardiac signals;
   a virtual load connected to said first electrode
   an active circuit, coupled to said second electrode and said virtual load, for providing electrical energy to said first electrode through said virtual load in response to the occurrence of a cardiac depolarization to counteract depolarization induced variation in the relative electrode/electrolyte equilibrium of said first and second electrodes;
   a monitoring circuit, coupled to said active circuit, for monitoring electrical energy provided through said virtual load, for detecting the occurrence of a cardiac depolarization;
   a capture detect timer defining a capture detect window after the generation of a pacing pulse by said pulse generator; and
   capture detect logic responsive to said monitoring circuit and said capture detect timer for detecting the occurrence of a cardiac depolarization accruing within said capture detect window.

2. The apparatus of claim 1 wherein said capture detect timer comprises:
   a first timer defining a first time interval following the generation of said pacing pulse; and
   a second timer defining a capture detect time window beginning with the expiration of said first time interval.

3. The apparatus of claim 2 wherein said first time interval is between 0 and 50 milliseconds.

4. The apparatus of claim 2 wherein said second capture detection time interval is between 30 and 100 milliseconds.

5. The apparatus of claim 1 wherein said virtual load provides a resistance between 0 and 1000 ohms.

6. The apparatus of claim 1 wherein said monitoring circuit comprises current monitoring circuitry for measuring the current through said virtual load.

7. The apparatus of claim 1 wherein said monitoring circuit comprises power measuring circuitry for measuring the power through said virtual load.

8. The apparatus of claim 1 further comprising auto threshold logic coupled to said pulse generator and responsive to said capture detect logic for altering the energy content of said pacing pulses in response to the occurrence or non-occurrence of a detected cardiac depolarization within said capture detect window.

9. The apparatus of claim 8 wherein said auto threshold logic increments the energy content of said pacing pulses in response to the non-occurrence of a detected cardiac depolarization within said capture detect window.

10. The apparatus of claim 1 wherein said means for applying pacing pulses to the heart comprises at least one of said first and second electrodes.

11. A cardiac pacemaker, comprising:
    a pulse generator for generating pacing pulses;
    means for applying said pacing pulses to cardiac tissue;
    means for detecting the depolarizations of cardiac tissue evoked by said pacing pulses, said detecting means comprising a first electrode means for location proximate said cardiac tissue, a second electrode, a virtual load connected to said first electrode, charge supplying means coupled to said virtual load and to said second electrode for maintaining said first electrode at a stead state of electrical potential relative to said second electrode and monitoring means for monitoring the current through said virtual load required to maintain said steady state during the occurrence of a cardiac depolarization;
    a capture detect timer defining a capture detect window after the generation of a pacing pulse by said pulse generator; and capture detect logic responsive to said monitoring circuit and said capture detect timer for detecting the occurrence of a cardiac depolarization occurring within said capture detect window.

12. A cardiac pacemaker according to claim 11 wherein said charge supplying means comprises an operational amplifier having inverting and noninverting inputs, and having an output, said charge supplying means further comprising a feedback impedance connected between said inverting input and said output, said noninverting input being connected to said second electrode means and said inverting input being connected to said virtual load.

* * * * *